US008586736B2

(12) United States Patent
Tian et al.

(10) Patent No.: US 8,586,736 B2
(45) Date of Patent: Nov. 19, 2013

(54) PERIMIDINE-BASED SQUARYLIUM DYE, DYE-CONTAINING COMPOSITION, AND IMAGE-FORMING MATERIAL

(75) Inventors: Minquan Tian, Kanagawa (JP); Takashi Matsubara, Kanagawa (JP); Suguru Nakaso, Kanagawa (JP); Yuka Ito, Kanagawa (JP); Shinji Hasegawa, Kanagawa (JP); Makoto Furuki, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 23 days.

(21) Appl. No.: 13/312,267

(22) Filed: Dec. 6, 2011

(65) Prior Publication Data
US 2012/0328975 A1 Dec. 27, 2012

(30) Foreign Application Priority Data

Jun. 23, 2011 (JP) ................................. 2011-139518

(51) Int. Cl.
*C07D 237/02* (2006.01)

(52) U.S. Cl.
USPC ........................................................ 544/224

(58) Field of Classification Search
USPC ............................................. 8/655; 430/105
See application file for complete search history.

(56) References Cited

U.S. PATENT DOCUMENTS 7,910,733 B2 * 3/2011 Tian et al. ..................... 544/249

FOREIGN PATENT DOCUMENTS

| JP | A-2007-248819 | | 9/2007 |
| JP | 2010-184980 | * | 8/2010 |
| JP | A-2010-184980 | | 8/2010 |

* cited by examiner

*Primary Examiner* — Andrew D Kosar
*Assistant Examiner* — John S Kenyon
(74) *Attorney, Agent, or Firm* — Oliff & Berridge, PLC

(57) ABSTRACT

A perimidine-based squarylium dye contains a compound represented by Formula (I),

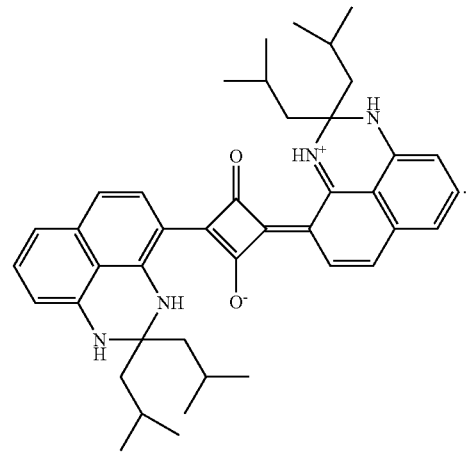

Formula (1)

the compound containing an isomer A and satisfying the following formula:

$Pa \geq 95(\%)$ wherein the isomer A is an isomer of the peak shown in the longest retention time among all peaks due to isomers obtained by analysis of the compound by means of reversed-phase high-performance liquid chromatography, and Pa represents a value of the peak area of the isomer A relative to the peak area of all peaks.

8 Claims, 2 Drawing Sheets

PERIMIDINE-BASED SQUARYLIUM DYE, DYE-CONTAINING COMPOSITION, AND IMAGE-FORMING MATERIAL

CROSS-REFERENCE TO RELATED APPLICATION

This application is based on and claims priority under 35 USC 119 from Japanese Patent Application No. 2011-139518 filed Jun. 23, 2011

BACKGROUND

Technical Field

The present invention relates to a perimidine-based squarylium dye, a dye-containing composition, and an image-forming material.

SUMMARY

According to an aspect of the invention, there is provided a perimidine-based squarylium dye containing a compound represented by Formula (I), Formula (1)

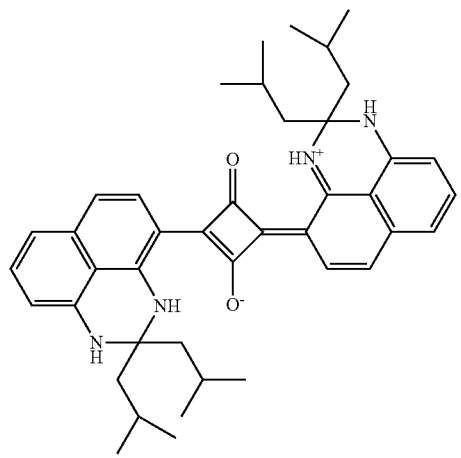

wherein the compound contains isomer A and satisfies the following formula:

Pa≥95(%)

wherein the isomer A is an isomer of the peak shown in the longest retention time among all peaks due to isomers obtained by analysis of the compound by means of reversed-phase high-performance liquid chromatography, and Pa represents a value of the peak area of the isomer A relative to the peak area of all peaks.

BRIEF DESCRIPTION OF THE DRAWINGS

Exemplary embodiments of the present invention will be described in detail based on the following figures, wherein.

DETAILED DESCRIPTION OF EMBODIMENTS

Figure 1:
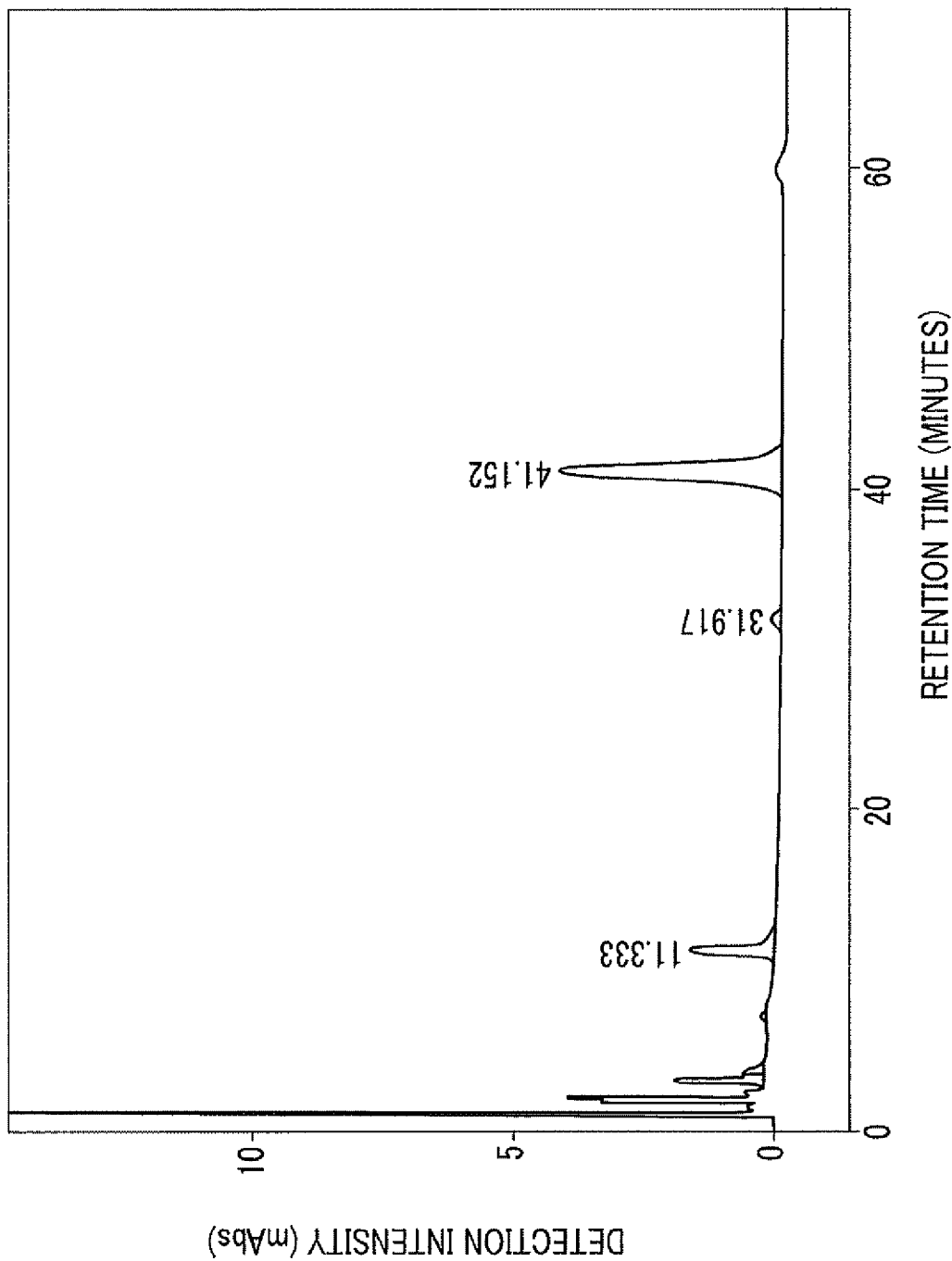
FIG. 1 is a graph illustrating the results of the analysis of the perimidine-based squarylium dye by reversed-phase high-performance liquid chromatography.

Hereinbelow, suitable exemplary embodiments of the invention will be described in detail.

[Perimidine-Based Squarylium Dye]

The perimidine-based squarylium dye according to the present exemplary embodiment is a perimidine-based squarylium dye containing a compound represented by the following Formula (I) (which may be sometimes hereinafter referred to as a "perimidine-based squarylium dye").

Formula (1)

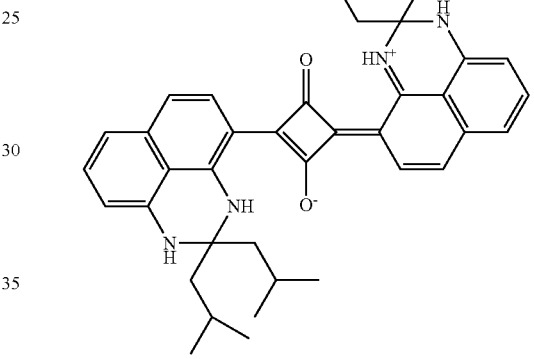

Furthermore, for the perimidine-based squarylium dye of the present exemplary embodiment, the peak area of the peak shown in the longest retention time (which may be sometimes hereinafter referred to as a "peak A") among all peaks derived from the perimidine-based squarylium dye obtained by analysis of the perimidine-based squarylium dye by means of reversed-phase high-performance liquid chromatography (which may be sometimes hereinafter referred to as "HPLC") is equal to or more than 95% of the peak area of all peaks derived from the perimidine-based squarylium dye.

More specifically, the compound contains an isomer A and satisfies the following formula:

Pa≥95(%)

wherein the isomer A is an isomer of the peak shown in the longest retention time among all peaks due to isomers obtained by analysis of the compound by means of reversed-phase high-performance liquid chromatography, and Pa represents a value of the peak area of the isomer A relative to the peak area of all peaks.

Moreover, for the perimidine-based squarylium dye according to the present exemplary embodiment, when the absorbance at a maximum absorption shown in the absorption wavelength in the range equal to or more than 802 nm and equal to or less than 808 nm is denoted as $A_{MAX}$, and the absorbances at the absorption wavelengths of 845 nm, 750 nm, 410 nm, and 345 nm are denoted as $A_{845}$, $A_{750}$, $A_{410}$, and $A_{345}$, respectively, in the absorption spectrum of a solution formed by dissolution in a mixed solvent containing 80% by volume of n-hexane and 20% by volume of tetrahydrofuran, the value of ($A_{845}/A_{MAX}$) is equal to or less than 0.059, the value of ($A_{750}/A_{MAX}$) is equal to or less than 0.21, the value of ($A_{410}/A_{MAX}$) is equal to or less than 0.043, and the value of ($A_{345}/A_{MAX}$) is equal to or less than 0.063.

That is, the compound satisfies the following formulae:

$$(A_{845}/A_{MAX}) \leq 0.059$$

$$(A_{750}/A_{MAX}) \leq 0.21$$

$$(A_{410}/A_{MAX}) \leq 0.043$$

$$(A_{345}/A_{MAX}) \leq 0.063$$

wherein $A_{MAX}$ represents an absorbance at a maximum absorption shown in the absorption wavelength in the range equal to or more than 802 nm and equal to or less than 808 nm, $A_{845}$ represents an absorbance of the absorption wavelength of 845 nm, $A_{750}$ represents an absorbance of the absorption wavelength of 750 nm, $A_{410}$ represents an absorbance of the absorption wavelength of 410 nm, and $A_{345}$ represents an absorbance of the absorption wavelength of 345 nm, in an absorption spectrum of a solution formed by dissolution of the compound in a mixed solvent comprising 80% by volume of n-hexane and 20% by volume of tetrahydrofuran.

The absorption spectrum of a solution formed by dissolution of the perimidine-based squarylium dye in a mixed solvent containing 80% by volume of n-hexane and 20% by volume of tetrahydrofuran is sometimes simply referred to as "the absorption spectrum of the perimidine-based squarylium dye".

Further, the value of ($A_{845}/A_{MAX}$), the value of ($A_{750}/A_{MAX}$), the value of ($A_{410}/A_{MAX}$), and the value of ($A_{345}/A_{MAX}$) are sometimes referred to "relative absorbance at 845 nm", "relative absorbance at 750 nm", "relative absorbance at 410 nm", and "relative absorbance at 345 nm", respectively.

<HPLC Analysis>

Hereinbelow, the HPLC analysis of the perimidine-based squarylium dye will be described.

In FIG. 1, the results of the analysis of the perimidine-based squarylium dye by HPLC are shown. The horizontal axis of the graph shown in FIG. 1 indicates retention time (minutes), and the vertical axis of the graph shown in FIG. 1 indicates a detection strength, specifically, an absorbance (mAbs) at a detection wavelength of 254 nm.

In the graph shown on FIG. 1, plural peaks derived from the perimidine-based squarylium dye are shown.

Specifically, plural peaks are constituted with a peak shown at a retention time of 42±2 minutes (which may be sometimes hereinafter referred to as a "peak A"), a peak shown at a retention time of 32±2 minutes (which may be sometimes hereinafter referred to as a "peak B"), and a peak shown at a retention time of 11±2 minutes (which may be sometimes hereinafter referred to as a "peak C"). Further, the retention time is a value obtained by rounding off to the whole number.

Moreover, it is thought that plural peaks (the peak A through the peak C) are derived from different isomers, respectively, among the perimidine-based squarylium dyes. That is, it is thought that three types of isomers are present in the perimidine-based squarylium dyes (an isomer showing the peak A, an isomer showing the peak B, and an isomer showing the peak C).

The isomer showing the peak A, the isomer showing the peak B, and the isomer showing the peak C may be sometimes hereinafter referred to as "isomer A", "isomer B", and "isomer C", respectively.

In the present exemplary embodiment, as described above, the proportion of the peak area of the peak A relative to the total peak area of plural peaks (the peak A, the peak B, and the peak C) is equal to or more than 95%. That is, the perimidine-based squarylium dye of the present exemplary embodiment contains the isomer A in an amount of equal to or more than 95% by mole among the isomers of the perimidine-based squarylium dye.

The perimidine-based squarylium dye containing the isomer A in an amount of equal to or more than 95% by mole may be sometimes hereinafter referred to as a "specific dye".

Further, the graph shown in FIG. 1 illustrates the results obtained from the HPLC analysis of a conventional perimidine-based squarylium dye (that is, an example of the perimidine-based squarylium dye other than the specific dye). Specifically, in FIG. 1, the proportion of the peak area of the peak A is 81.0%, the proportion of the peak area of the peak B is 2.6%, and the proportion of the peak area of the peak C is 16.4%.

The analysis method by HPLC mentioned above is as follows.

First, the perimidine-based squarylium dye is dissolved in tetrahydrofuran (THF) to prepare a THF solution at a concentration equal to or less than $1 \times 10^{-4}$ mol/L. Further, as THF for the solvent, for example, THE for HPLC is used. In addition, in the preparation of the THF solution, the THF solution may be irradiated with ultrasonic waves for 30 minutes in order to dissolve the perimidine-based squarylium dye.

As the analysis apparatus, for example, a reversed-phase high-performance liquid chromatography apparatus (HPLC apparatus, Product No.: LC-10A, manufactured by Shimadzu Corporation) is used.

As the column for HPLC, an octadecylsilyl column (ODS column) is used, and specific examples thereof include a product that is manufactured by Chemco Scientific Co., Ltd. and has a spec such as product name: CHEMCOSORB, model No.: 5-ODS-H, inner diameter: 4.6 mm, length: 150 mm. Herein, the octadecylsilyl column refers to a column packed with chemically-bonded porous spherical silica gel, which is surface-modified with octadecylsilyl groups, as a stationary phase.

Furthermore, the measurement conditions may be, for example, the condition of a column temperature of 45° C., an injection amount of measurement sample of 10 μl, a flow rate of measurement sample of 1 ml/min, a detection wavelength of 254 nm, and a mobile phase of a mixed solution of acetonitrile and water (volume ratio of acetonitrile:water=8:2).

Examples of the method for subjecting the perimidine-based squarylium dye included in the dye-containing composition or image-forming material to HPLC analysis include a method in which a dye-containing composition or image-forming material is dissolved in a solvent, and HPLC analysis is carried out as described above.

<Absorption Spectrum>

Hereinbelow, the absorption spectrum of the perimidine-based squarylium dye will be described.

Figure 2:
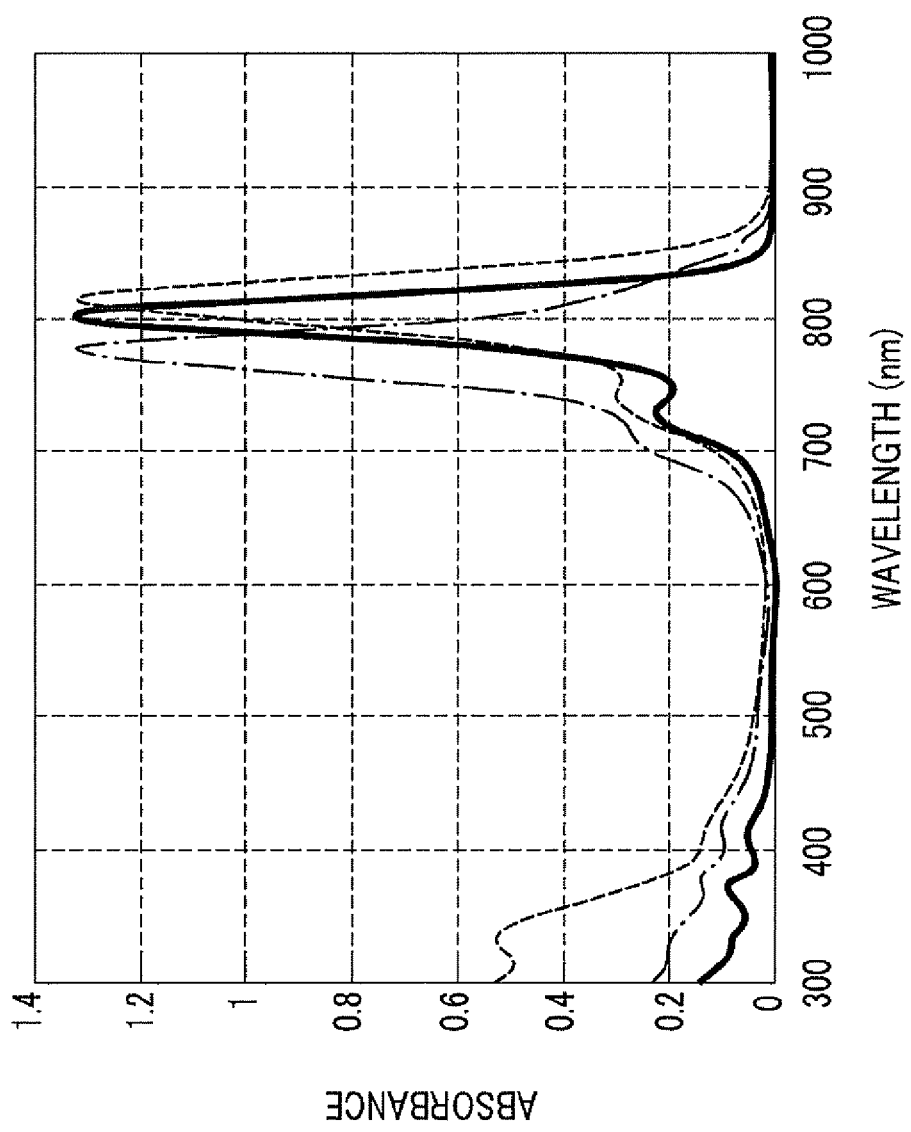
FIG. 2 is a diagram illustrating the absorption spectrum (solid line) of the perimidine-based squarylium dye showing the peak A (a peak having a retention time of 41.152 minutes) of FIG. 1; the absorption spectrum (dotted line) of the perimidine-based squarylium dye showing the peak B (a peak having a retention time of 31.917 minutes) of FIG. 1; and the absorption spectrum (dashed line) of the perimidine-based squarylium dye showing the peak C (a peak having a retention time of 11.333 minutes) of FIG. 1.

In FIG. 2, the results of measurement of the absorption spectrum of a solution formed by dissolution in a mixed solvent including 80% by volume of n-hexane and 20% by volume of tetrahydrofuran, with respect to each of 3 isomers of the perimidine-based squarylium dyes are also shown in combination.

Specifically, the absorption spectrum of the isomer A (solid line in FIG. 2), the absorption spectrum of the isomer B (dotted line in FIG. 2), and the absorption spectrum of the isomer C (dashed line in FIG. 2) are shown in FIG. 2.

In addition, in FIG. 2, the $A_{MAX}$ in the absorption spectrum of the isomer A, the $A_{MAX}$ in the absorption spectrum of the isomer B, and the $A_{MAX}$ in the absorption spectrum of the isomer C are all the same values.

As shown in FIG. 2, in the absorption spectrum of the isomer A (that is, the absorption spectrum of a specific dye having 100% by mole of the isomer A), the absorption wavelength at the maximum absorption is 805 nm, and the relative absorbances at 845 nm, 750 nm, 410 nm, and 345 nm are 0.047, 0.19, 0.040, and 0.047, respectively.

Furthermore, the values of $A_{845}$, $A_{750}$, $A_{410}$, and $A_{345}$ in the absorption spectrum of the isomer B and the isomer C shown in FIG. 2 are all values higher than the corresponding ones of $A_{845}$, $A_{750}$, $A_{410}$, and $A_{345}$ in the absorption spectrum of the isomer A.

Accordingly, it is thought that as the proportion of the isomer A is lower, the proportion of the isomer B and the isomer C is relatively higher, and as a result, at any of 845 nm, 750 nm, 410 nm, and 345 nm, the relative absorbance increases.

Moreover, since the proportion of the isomer A is equal to or more than 95% by mole in the specific dye of the present exemplary embodiment, the relative absorbances at 845 nm, 750 nm, 410 nm, and 345 nm are equal to or less than 0.059, equal to or less than 0.21, equal to or less than 0.043, and equal to or less than 0.063, respectively.

Further, the absorption spectrum shown in FIG. 2 is measured in the following manner. Specifically, first, the solvent is removed from the solution of the isomer A, the isomer B, and the isomer C separated by the HPLC analysis to obtain an isomer A, an isomer B, and an isomer C, respectively. Next, a solution obtained by dissolving 5 mg of the isomer A in 100 ml of the mixed solvent, a solution obtained by dissolving 5 mg of the isomer B in 200 ml of the mixed solvent, and a solution obtained by dissolving 5 mg of the isomer C in 300 ml of the mixed solvent are prepared, and measurement is carried out under the conditions of 25° C. using a spectrophotometer (Product No.: U4100, manufactured by Hitachi High-Technologies Corporation).

In the case of determining the values of $A_{MAX}$, $A_{845}$, $A_{750}$, $A_{410}$, and $A_{345}$ of the perimidine-based squarylium dye, the absorption spectrum is measured in the same manner as in the method, and the values of the $A_{MAX}$, $A_{845}$, $A_{750}$, $A_{410}$, and $A_{345}$ are determined.

Furthermore, examples of the method for measuring the absorption spectrum of the perimidine-based squarylium dye included in the dye-containing composition or the image-forming material as described later include a method in which a perimidine-based squarylium dye is extracted from a dye-containing composition or an image-forming material, and the absorption spectrum of the perimidine-based squarylium dye thus obtained is measured by the same method as above.

For example, in the case where the image-forming material is an electrophotographic toner, only a perimidine-based squarylium dye is extracted from a toner and the absorption spectrum is measured by the above method above, by performing separation and purification by means of gel permeation chromatography (GPC).

The perimidine-based squarylium dye of the present exemplary embodiment as described above (that is, a specific dye) has low absorption in a visible region, as compared with a case of a perimidine-based squarylium dye other than the specific dye (that is, a perimidine-based squarylium dye having a proportion of the isomer A of less than 95%). The reason is presumed to be as follows: since the isomer B and the isomer C have relatively higher absorption in the visible region at equal to or more than 400 nm and equal to or less than 750 nm (which may be sometimes hereinafter simply referred to as a "visible region"), as compared with the isomer A as described above, the proportion of the isomer B and the isomer C included in the perimidine-based squarylium dye is lowered by including the isomer A in an amount of equal to or more than 95% by mole, and as a result, the perimidine-based squarylium dye having low absorption in a visible region is provided.

Furthermore, when the specific dye is used in an image-forming material, an image in which the perimidine-based squarylium dye is hardly visible, as compared with a case where a perimidine-based squarylium dye other than the specific dye is used, can be obtained.

Specifically, for example, in the case of an image-forming material not using a color material other than the perimidine-based squarylium dye (which may be sometimes hereinafter referred to as "other color materials"), when an image is formed using the image-forming material of the present exemplary embodiment, the image itself is hardly visible (that is, an image having excellent invisibility can be obtained), as compared with a case where an image is formed using an image-forming material containing a perimidine-based squarylium dye other than the specific dye.

On the other hand, for example, in the case of using another color material (particularly, a color material having absorption in the visible region) for the purpose of coloring the image-forming material, the color of the image-forming material is not easily disturbed and desired color is easily maintained by the perimidine-based squarylium dye by using the image-forming material of the present exemplary embodiment, as compared with a case where an image-forming material containing a perimidine-based squarylium dye other than the specific dye is used.

Furthermore, the perimidine-based squarylium dye is a dye having a high absorbance in an infrared region which is in a range of more than 750 nm and equal to or less than 1000 nm (which may be sometimes hereinafter simply referred to as an "infrared region"). For this reason, if the image-forming material of the present exemplary embodiment is used, an image is formed in which the perimidine-based squarylium dye is hardly visible, and further, light in the infrared region is easily absorbed.

Therefore, for example, by using the image-forming material of the present exemplary embodiment and irradiating the image-forming material with infrared light at a wavelength equal to or more than 760 nm and equal to or less than 900 nm to fix the image-forming material onto a recording medium or the like, thereby forming an image, an image which secures fixability and has a hardly-visible perimidine-based squarylium dye can be obtained.

Furthermore, for example, in the case where invisible information is recorded using the image-forming material of the present exemplary embodiment, invisible information having compatibility between invisibility of the information and easy readability of the invisible information by light in the infrared region (particularly infrared light in the range of 815 nm±35 nm) is obtained.

Further, in the present specification, the "invisibility" refers to being hardly recognizable with the naked eye in visible light (that is, ideally invisible).

Moreover, the dye-containing composition using the specific dye has low absorption in the visible region and has a hardly-visible perimidine-based squarylium dye, as compared with a dye-containing composition using a perimidine-based squarylium dye other than the specific dye.

In this regard, for example, if the dye-containing composition of the present exemplary embodiment is used as a paint for generating heat by absorption of infrared rays, a coating film having a hardly-visible perimidine-based squarylium dye can be obtained, as compared with a case using a perimidine-based squarylium dye other than the specific dye. In addition, for example, if the dye-containing composition of the present exemplary embodiment is used for an infrared light filter for shielding infrared rays with the transmittance of visible light, an infrared light filter having high transmittance in the visible region can be obtained, as compared with a case using a perimidine-based squarylium dye other than the specific dye.

Furthermore, the perimidine-based squarylium dye has a high absorbance in the infrared region as described above. Accordingly, for example, by using the dye-containing composition of the present exemplary embodiment as the paint, a coating film having a hardly-visible perimidine-based squarylium dye and easy absorption of the infrared light can be obtained. Furthermore, for example, by using the dye-containing composition of the present exemplary embodiment in the infrared light filter, an infrared light filter having compatibility between high transmittance in the visible region and high absorption rate in the infrared region can be obtained.

In the present exemplary embodiment, as described above, the proportion of the isomer A relative to the total perimidine-based squarylium dye is equal to or more than 95% by mole, but a higher proportion of the isomer A is preferable, the proportion of the isomer A is more preferably equal to or more than 99% by mole, and most preferably 100% by mole.

That is, in the present exemplary embodiment, in the HPLC analysis, the proportion of the peak area of the peak A, relative to the sum of the peak area of all peaks derived from the perimidine-based squarylium dye is equal to or more than 95%, and a higher proportion of the peak area of the peak A is preferable, and the peak area of the peak A is more preferably equal to or more than 99%, and most preferably 100%.

In addition, in the present exemplary embodiment, in the absorption spectrum of the perimidine-based squarylium dye as described above, the relative absorbances at 845 nm, 750 nm, 410 nm, and 345 nm are equal to or less than 0.059, equal to or less than 0.21, equal to or less than 0.043, and equal to or less than 0.063, respectively, and values closer to the relative absorbance of the isomer A itself are preferable, and the relative absorbances are more preferably equal to or less than 0.051, equal to or less than 0.20, equal to or less than 0.041, and equal to or less than 0.062, respectively.

<Method for Producing Perimidine-Based Squarylium Dye>

Hereinbelow, a method for producing the perimidine-based squarylium dye (a specific dye) according to the present exemplary embodiment will be described.

The method for producing the specific dye is not particularly limited, but examples thereof include a method in which a perimidine-based squarylium dye is prepared by a conventional method, then isomers are separated by, for example, column chromatography or the like (which may be sometimes hereinafter referred to as a "separation process") to obtain a specific dye (which may be sometimes hereinafter referred to as "first production method"), a method in which a specific solvent is used for the reaction of a perimidine intermediate as described later with squaric acid (Process (A-2) as described later) to obtain a specific dye without separation process (which may be sometimes hereinafter referred to as "second production method"), and the like.

By using the first production method, the proportion of the isomer A in the specific dye is easily controlled, as compared with a case using the second production method. On the other hand, by using the second production method, there is no need to carry out the separation process, as compared with a case using the first production method, thus the production process of the specific dye becomes simple, and the specific dye can be easily obtained.

Further, the specific dye obtained by the second production method may be further subjected to separation of isomers by the separation process.

(First Production Method)

First, the first production method will be described.

The first production method is a method in which a perimidine-based squarylium dye other than the specific dye is obtained by a conventional synthesis method as described above, and then the isomers are separated by a separation process to obtain a specific dye.

Hereinbelow, the method for obtaining a perimidine-based squarylium dye by the conventional method will be described.

—Synthesis of Perimidine-Based Squarylium Dye—

The compound represented by Formula (I) is synthesized by, for example, the following processes.

Specifically, the perimidine intermediate (a) can be obtained by reacting 1,8-diaminonaphthalene with 2,6-dimethyl-4-heptanone in the presence of a catalyst under the condition of azeotropic reflux in a solvent (Process (A-1)).

Examples of the catalyst that is used in Process (A-1) include p-toluenesulfonic acid monohydrate, benzenesulfonic acid monohydrate, 4-chlorobenzenesulfonic acid hydrate, pyridine-3-sulfonic acid, ethanesulfonic acid, sulfuric acid, nitric acid, acetic acid, and the like.

Further, examples of the solvent that is used in Process (A-1) include alcohols, aromatic hydrocarbons, and the like.

The perimidine intermediate (a) is purified by, for example, high-performance column chromatography or recrystallization.

Next, the perimidine intermediate (a) can be reacted with 3,4-dihydroxycyclobuta-3-ene-1,2-dione (also referred to as "squaric acid" or "quadratic acid") under the condition of azeotropic reflux in a solvent to obtain a compound represented by Formula (I) (Process (A-2)). Process (A-2) is performed, for example, under a nitrogen gas atmosphere.

Examples of the solvent that is used in Process (A-2) include alcohols such as 1-propanol, 1-butanol, 1-pentanol, and the like, aromatic hydrocarbons such as benzene, toluene, xylene, monochlorobenzene, and the like, ethers such as tetrahydrofuran, dioxane, and the like, halogenated hydrocarbons such as chloroform, dichloroethane, trichloroethane, dichloropropane, and the like, and amides such as N,N-dimethylformamide, N,N-dimethylacetamide, and the like. Although alcohols may be used alone, other solvents such as aromatic hydrocarbons, ethers, halogenated hydrocarbons, amides, and the like may be used in a mixture with alcohols.

As the solvent that is used in Process (A-2), 1-propanol, 2-propanol, 1-butanol, 2-butanol, a mixed solvent of 1-propanol and benzene, a mixed solvent of 1-propanol and toluene, a mixed solvent of 1-propanol and N,N-dimethylformamide, a mixed solvent of 2-propanol and benzene, a mixed solvent of 2-propanol and toluene, a mixed solvent of 2-propanol and N,N-dimethylformamide, a mixed solvent of 1-butanol and benzene, a mixed solvent of 1-butanol and toluene, a mixed solvent of 1-butanol and N,N-dimethylformamide, a mixed solvent of 2-butanol and benzene, a mixed solvent of 2-butanol and toluene, or a mixed solvent of 2-butanol and N,N-dimethylformamide may be used. When such a mixed solvent is used, the concentration of the alcohols may be equal to or more than 1% by volume, and is more preferably equal to or more than 5% and equal to or less than 75% by volume.

Moreover, the mole ratio of the perimidine intermediate (a) to 3,4-dihydroxycyclobuta-3-ene-1,2-dione (the number of moles of the perimidine intermediate (a)/the number of moles of 3,4-dihydroxycyclobuta-3-ene-1,2-dione) in Process (A-2) may be, for example, equal to or more than 1 and equal to or less than 4, and preferably equal to or more than 1.5 and equal to or less than 3.

Furthermore, in Process (A-2), a dehydrating agent may be used. The dehydrating agent is not particularly limited as long as it reacts with neither the perimidine intermediate (a) nor 3,4-dihydroxycyclobuta-3-ene-1,2-dione, but examples thereof include orthoformates such as trimethyl orthoformate, triethyl orthoformate, tripropyl orthoformate, tributyl orthoformate, and the like, a molecular sieve, etc.

Although the reaction temperature in Process (A-2) varies depending on the kind of the solvent used, the temperature of the reaction solution may be, for example, equal to or higher than 60° C., and more preferably equal to or higher than 75° C. For example, in the case of using a mixed solvent of 1-butanol and toluene, the temperature of the reaction solution may be, for example, equal to or higher than 75° C. and equal to or lower than 105° C.

In addition, the reaction time in Process (A-2) varies depending on the kind of the solvent or the temperature of the reaction solution. For example, in the case where the reaction is carried out under conditions that a mixed solvent of 1-butanol and toluene is used and the temperature of the reaction solution is equal to or higher than 90° C. and equal to or lower than 105° C., the reaction time may be, for example, equal to or more than 2 hours and equal to or less than 4 hours.

In this manner, a perimidine-based squarylium dye is synthesized.

Further, the compound (perimidine-based squarylium dye) produced in Process (A-2), which is represented by Formula (I), may be purified by washing with a solvent or recrystallization.

The solvent used for washing is not particularly limited, and specific examples thereof include alcohols, acetone, acetonitrile, THF, tetrahydropyran, diisopropyl ether, chloroform, chlorobenzene, ethyl formate, ethyl acetate, and the like.

—Separation Process—

Next, the separation process will be described. The separation process is not particularly limited as long as it is a method capable of separating the isomers of the perimidine-based squarylium dye to obtain a specific dye, but examples thereof include a method for separating isomers by column chromatography. Further, in the case of separating isomers by column chromatography, examples of the types of the column to be used include silica gel column, alumina column, and the like.

The process for separating isomers by column chromatography is carried out, for example, as follows.

Specifically, first, for example, silica gel 60N (spherical, neutral, particle diameter 63 to 210 μm) (manufactured by Kanto Chemical Co., Ltd., Product No.: 37565-84) is used as a column packing material, to prepare a packed cylindrical column having an inner diameter of 65 mm and a length of 15 cm.

Next, n-hexane is used as a developing solvent to rinse the column filler, and then a dye solution in which 1 g of the perimidine-based squarylium dye to be separated is dissolved in 15 ml of acetone is adhered to about 40 g of silica gel 60N, followed by volatilization of acetone, and the residue is added to the packed column.

Thereafter, n-hexane, a mixed solvent including 90% by volume of n-hexane and 10% by volume of THF, a mixed solvent including 85% by volume of n-hexane and 15% by volume of THF, and a mixed solvent including 80% by volume of n-hexane and 20% by volume of THF are flowed sequentially as developing solvents into the column. After components showing a maximum absorption at 802 nm through 808 nm are collected while checking the absorption spectrum of the eluate, the solvent is removed by distillation under reduced pressure, and the black-brown solid thus obtained is further recrystallized from a mixed solvent of acetone and n-hexane to give a specific dye.

(Second Production Method)

Next, the second production method will be described.

The second production method is a method in which a specific solvent is used as the solvent for the process of reacting the perimidine intermediate and squaric acid (Process (A-2)) in a synthesis method for the perimidine-based squarylium dye as described above, to obtain a specific dye.

Examples of the specific solvent used in Process (A-2) include a mixed solvent including an alcohol having a permittivity at 25° C. (which may be sometimes hereinafter simply referred to as "permittivity") equal to or less than 16 $Fm^{-1}$ and a low-polarity compound or nonpolar compound having a permittivity equal to or less than 3 $Fm^{-1}$.

The mixed solvent may contain a solvent other than an alcohol having a permittivity in the above-described range and a low-polarity compound or nonpolar compound having a permittivity in the above-described range, but preferably does not contain it. Particularly, in the case where the alcohol having a permittivity outside the above-described range (that is, an alcohol having high polarity) is preferably not contained in the mixed solvent, the specific dye can be easily obtained, and if contained, preferably it is in an amount equal to or less than 3% by mass.

Examples of the alcohol having a permittivity in the above-described range include 1-hexanol, benzyl alcohol, 1-pentanol, isopentyl alcohol, cyclohexanol, 3-methylcyclohexanol, 4-methylcyclohexanol, 1-heptanol, 2-heptanol, 1-octanol, and the like, and the alcohols may be used singly or in combination of two or more kinds thereof. Further, the permittivity of the alcohol may be equal to or less than 16 $Fm^{-1}$, equal to or less than 15 $Fm^{-1}$, or equal to or less than 14 $Fm^{-1}$.

Examples of the low-polarity compound or nonpolar compound include toluene, benzene, ethylbenzene, xylene, methylcyclohexane, ethylcyclohexane, octane, nonane, and the like, and the low-polarity compound or nonpolar compound may be used singly or in combination of two or more kinds thereof. Further, the permittivity of the low-polarity compound or nonpolar compound may be equal to or less than 3 $Fm^{-1}$, or equal to or less than 2 $Fm^{-1}$.

Specific examples of the mixed solvent include a mixed solvent of 1-hexanol and toluene, a mixed solvent of 1-octanol and toluene, a mixed solvent of 1-heptanol and methylcyclohexane, and the like.

The content of the alcohol having a permittivity in the above-described range in the mixed solvent may be, for example, equal to or more than 1% by mass and equal to or less than 30% by mass, or equal to or more than 3% by mass and equal to or less than 20% by mass.

By using the above-described mixed solvent as a solvent in Process (A-2) and carrying out the synthesis method for the perimidine-based squarylium dye as described in the first production method, the specific dye can be obtained. Further, as described above, the specific dye obtained by the second production method may be subjected to isomer separation by the separation process to obtain a specific dye having a high proportion of the isomer A.

Examples of the method for obtaining particles of the specific dye include a method in which the specific dye obtained in the first production method, the second production method, or the like is dissolved in tetrahydrofuran, the solution is injected by an injector while stirring into ice-cooled distilled water, to produce precipitates, and the precipitate is collected by suction filtration, washed with distilled Water, and dried in vacuo. Herein, the particle diameter of the obtained precipitate is regulated by adjusting the concentration of the specific dye in the solution, the injection rate of the solution, the amount or temperature of distilled water, and the stirring speed, or the like.

Furthermore, particles of the specific dye may be obtained by a milling treatment. Specifically, for example, by putting the specific dye, tetrahydrofuran, and zirconia beads into a vessel for ball milling, and carrying out a milling treatment, particles of the specific dye can be obtained.

The volume-weighted average particle diameter of the particles of the specific dye may be, for example, equal to or more than 10 nm and equal to or less than 300 nm, or equal to or more than 20 nm and equal to or less than 200 nm.

[Dye-Containing Composition and Image-forming Material]

The application of the dye-containing composition of the present exemplary embodiment is not particularly limited, but specific examples of the application include, in addition to an image-forming material as described later, a paint for a heat-generating product which generates heat by absorption of infrared light, a composition for forming a filter film for an infrared light filter transmitting visible light and shielding infrared rays, and the like.

The dye-containing composition of the present exemplary embodiment is not particularly limited as long as it contains the perimidine-based squarylium dye (the specific dye) of the exemplary embodiment, but it may contain other components according to the purposes.

Hereinbelow, as an example of the dye-containing composition of the present exemplary embodiment, the image-forming material of the present exemplary embodiment will be described.

The image-forming material of the present exemplary embodiment contains the specific dye as described above, and if necessary, may further contain components other than the specific dye.

The content of the specific dye in the total image-forming materials may be, for example, equal to or more than 0.05% by mass and equal to or less than 3% by mass (or from about 0.05% by mass to about 3% by mass), or equal to or more than 0.1% by mass and equal to or less than 2% by mass.

The image-forming material may contain the specific dye in the form of particles. Examples of the particles of the specific dye contained in the image-forming material include those having volume-weighted average particle diameters in the range described above.

The application of the image-forming material in the present exemplary embodiment is not particularly limited, but examples thereof include an electrophotographic toner, an ink-jet printer ink, an ink for typographic printing, offset printing, flexographic printing, gravure printing, or silk printing, and the like.

In the case where the image-forming material of the present exemplary embodiment is an electrophotographic toner (which may be sometimes hereinafter referred to as a "toner"), the image-forming material may be used by itself as a single-component developer, or may be used as a two-component developer in combination with a carrier.

Examples of the carrier include a resin-coated carrier having a resin-coated layer on a core material, and in this resin-coated layer, electrically conductive powder or the like may be dispersed.

Furthermore, when the image-forming material of the present exemplary embodiment is a toner, the image-forming material may contain a binder resin. Examples of a binder resin include homopolymers or copolymers synthesized from styrenes such as styrene, chlorostyrene, and the like, monoolefins such as ethylene, propylene, butylene, isoprene, and the like, vinyl esters such as vinyl acetate, vinyl propionate, vinyl benzoate, vinyl butyrate, and the like, α-methylene aliphatic monocarboxylic acid esters such as methyl acrylate, ethyl acrylate, butyl acrylate, dodecyl acrylate, octyl acrylate, phenyl acrylate, methyl methacrylate, ethyl methacrylate, butyl methacrylate, dodecyl methacrylate, and the like, vinyl ethers such as vinyl methyl ether, vinyl ethyl ether, vinyl butyl ether, and the like, and vinyl ketones such as vinyl methyl ketone, vinyl hexyl ketone, vinyl isopropenyl ketone, and the like.

Among these, examples of the especially typical binder resins include a polystyrene, a styrene-alkyl acrylate copolymer, a styrene-alkyl methacrylate copolymer, a styrene-acrylonitrile copolymer, a styrene-butadiene copolymer, a styrene-maleic anhydride copolymer, polyethylene, polypropylene, and the like.

In addition, a polyester, a polyurethane, an epoxy resin, a silicone resin, a polyamide, a modified rosin, a paraffin wax, or the like may also be used as a binder resin.

Furthermore, in the case where the image-forming material of the present exemplary embodiment is a toner, for example, the toner is irradiated with infrared light at equal to or more than 760 nm and equal to or less than 900 nm and fixed onto a recording medium or the like to form a fixed image, and a thermoplastic resin may be used as a binder resin. It is thought that when the thermoplastic resin is used, in the process in which a toner is fixed onto a recording medium, the specific dye absorbs infrared light irradiated onto the toner to generate heat, the heat allows the thermoplastic resin to be melted, and thus, the toner is fixed on the recording medium.

As the thermoplastic resin, a thermoplastic resin containing a naturally occurring polymer or a synthetic polymer may be used without particular restriction. Further, specific examples of the thermoplastic resin include an epoxy resin, a styrene-acrylic resin, a polyamide resin, a polyester resin, a polyvinyl resin, a polyolefin resin, a polyurethane resin, a polybutadiene resin, and the like, and these may be used singly or in a mixture of two or more kinds thereof. Among these thermoplastic resins, particularly, examples of the thermoplastic resin with which the specific dye is easily dispersed in the toner and a toner having high thermal fixing efficiency can be obtained include a styrene-acrylic resin and a polyester resin.

The weight-average molecular weight of the thermoplastic resin may be, for example, equal to or more than 1000 and equal to or less than 100000, or equal to or more than 5000 and equal to or less than 50000 or less.

In addition, the glass transition temperature of the thermoplastic resin may be, for example, equal to or higher than 50° C. and equal to or lower than 150° C., or equal to or higher than 55° C. and equal to or lower than 70° C.

In the case where the image-forming material of the present exemplary embodiment is a toner, the image-forming material may not contain other color materials (for example, a pigment and the like), or may contain other color materials, if necessary.

Furthermore, in the case where the image-forming material of the present exemplary embodiment is a toner, the image-forming material may contain a charge-controlling agent, a release agent, and the like, if necessary.

The charge-controlling agent includes those which are used in positive (+) charging and those which are used in negative (−) charging. Examples of the charge-controlling agent which is used in positive (+) charging include quaternary ammonium-based compounds. Further, examples of the charge-controlling agent which is used in negative (−) charging include metal complexes of alkylsalicylic acid, charge-controlling agents of polar group-containing resin type, and the like. Examples of the release agent include a low-molecular-weight polyethylene, a low-molecular-weight polypropylene, and the like.

Moreover, in the case where the image-forming material of the present exemplary embodiment is a toner, the image-forming material may be one in which inorganic particles or organic particles are added as an external additive to the surface of the toner particle. Examples of the inorganic particles include silica, alumina, titania, calcium carbonate, magnesium carbonate, calcium phosphate, cerium oxide, and the like. Further, a surface treatment may be given to those inorganic particles in accordance with the purposes. Examples of the organic particles include emulsion polymers containing polyvinylidene fluoride, polymethyl methacrylate, styrene-methyl methacrylate copolymer, or the like, soap-free polymers (emulsion polymers with no emulsifier), and the like.

In the case where the image-forming material of the present exemplary embodiment is a toner, the image-forming material is prepared by a general production method for a toner. Examples of the production method for the toner include a method in which a binder resin including necessary materials is melt-kneaded and pulverized (kneading/pulverizing method), a method in which a polymerizable monomer including necessary materials is polymerized in a solution to directly obtain a toner, a method in which a monomer including necessary materials is polymerized in a solution and aggregated to obtain a toner, a method in which a monomer is polymerized, and then aggregated with necessary materials, a method in which a binder resin is dispersed in a particle solution and aggregated with necessary materials, and the like.

In the case where the image-forming material of the present exemplary embodiment is an ink for an ink-jet printer, the image-forming material may be in the form of an aqueous water-containing ink. Furthermore, in the case where the image-forming material is an aqueous ink, it may further contain a water-soluble organic solvent so as to prevent drying of the ink and to improve the permeability of the ink.

Examples of the water include ion exchange water, ultrafiltered water, pure water, and the like.

Moreover, examples of the organic solvent include polyhydric alcohols such as ethylene glycol, diethylene glycol, polyethylene glycol, glycerin, and the like; N-alkyl pyrrolidones; esters such as ethyl acetate, amyl acetate, and the like; lower alcohols such as methanol, ethanol, propanol, butanol, and the like; and glycol ethers such as ethylene oxide or propylene oxide adducts of methanol, butanol, and phenol, and the like. These organic solvents may be used singly or in combination of two or more kinds thereof.

The organic solvent may be appropriately selected in consideration of hygroscopicity, moisture-retaining properties, the solubility of the perimidine-based squarylium dye, permeability, ink viscosity, freezing point, and the like. The content of the organic solvent in the ink for an ink-jet printer may be, for example, equal to or more than 1% by weight and equal to or less than 60% by weight.

In addition, in the case where the image-forming material of the present exemplary embodiment is an ink for an ink-jet printer, the image-forming material may contain additives, if necessary. Examples of the additives include a pH adjuster, a specific resistance adjuster, an antioxidant, a preservative, a mildew-proofing agent, a metal-sequestering agent, and the like.

Examples of the pH adjuster include alcohol amines, ammonium salts, metal hydroxides, and the like. Examples of the specific resistance adjuster include organic salts and inorganic salts. Further, examples of the metal-sequestering agent include a chelating agent and the like.

Furthermore, in the case where the image-forming material of the present exemplary embodiment is an ink for an ink-jet printer, a water-soluble resin such as polyvinyl alcohol, polyvinyl pyrrolidone, carboxymethyl cellulose, a styrene-acrylic acid resin, a styrene-maleic acid resin, and the like may be contained in the image-forming material in such an amount as not to cause clogging of a spray and sealing nozzle or variance of an ink-jetting direction, and the like.

Furthermore, in the case where the image-forming material of the present exemplary embodiment is an ink for typographic printing, offset printing, flexographic printing, gravure printing, or silk printing, the image-forming material may be in the form of an oil ink containing a polymer or an organic solvent.

Examples of the polymer include natural resins such as proteins, rubbers, celluloses, shellac, copal, starch, rosin, and the like; thermoplastic resins such as a vinyl resin, an acrylic resin, a styrene resin, a polyolefin resin, a novolak-type phenol resin, and the like; and thermosetting resins such as a resol-type phenol resin, an urea resin, a melamine resin, a polyurethane resin, an epoxy resin, an unsaturated polyester, and the like.

Further, examples of the organic solvent include those described above as examples of organic solvents exemplified for the ink for an ink-jet printer.

Furthermore, in the case where the image-forming material of the present exemplary embodiment is an ink for typographic printing, offset printing, flexographic printing, gravure printing or silk printing, the image-forming material may further contain an additive such as a plasticizer for improving the flexibility or strength of a printed film, a solvent for adjusting the viscosity, or improving the drying properties, a desiccant, a viscosity adjuster, a dispersant, various kinds of reactants, and the like.

Moreover, the image-forming material of the present exemplary embodiment may further contain a stabilizer. The stabilizer should receive energy from the specific dye in an excited state and preferably has an absorption band at the longer wavelength side than the absorption band in the infrared region of the specific dye. In addition, examples of the stabilizer include a stabilizer that resists decomposition by singlet oxygen and has high compatibility with the specific dye. Specific examples of such a stabilizer include a metalloorganic complex compound, and more specifically, include a compound represented by the following general formula (4).

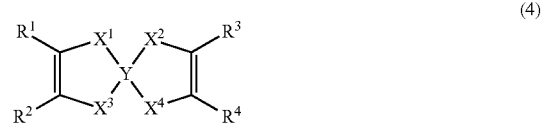

In the general formula (4), $R^1$ to $R^4$ may be the same as or different from each other, and each represents a substituted or unsubstituted phenyl group. When the phenyl group represented by any of $R^1$ to $R^4$ has a substituent, examples of the substituent include H, $NH_2$, OH, $N(C_hH_{2h+1})_2$, $OC_hH_{2h+1}$, $C_hH_{2h-1}$, $C_hH_{2h+1}$, $C_hH_{2h}OH$, or $C_hH_{2h}OC_iH_{2i+1}$ (wherein h represents an integer from 1 to 18 and i represents an integer from 1 to 6), and the like. Further, $X^1$ to $X^4$ may be the same as or different from each other, and each represent O, S, or Se, and Y represents a transition metal such as Ni, Co, Mn, Pd, Cu, Pt, and the like.

As a specific example of the compounds represented by the general formula (4), a compound represented by the following formula (5) is particularly preferable.

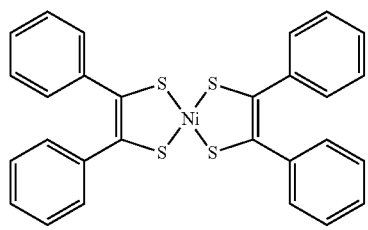

(5)

The amount of the stabilizer to be added may be equal to or more than about 1/10 and equal to or less than 2 times the mass of the specific dye.

The image-forming material of the present exemplary embodiment can be obtained, for example, by mixing the specific dye with other components as described above.

The image-forming material of the present exemplary embodiment may be used for the purpose of, for example, irradiating the image-forming material with infrared light at equal to or more than 760 nm and equal to or less than 900 nm to fix the image-forming material onto a recording medium or the like to form a fixed image as described above.

Typical examples of the light source of the infrared light include a semiconductor laser, a solid laser, a liquid laser, a gas laser, and the like. Specific examples of widely used lasers include a GaAs semiconductor laser, which emits light at a wavelength of 808 nm.

Examples of the recording medium include paper, plastic media such as a card, an optical recording medium and the like, cloth, a metal plate, and the like. The material properties or the characteristics of the recording medium may be selected within a range that can resist heat during the fixing.

Examples of the method for applying the image-forming material on the recording medium include an electrophotographic method, an ink-jet method, a typographical printing method, an offset printing method, a flexographic printing method, a gravure printing method, a silk printing method, and the like. Among these, examples of the method suitable for heating by irradiation with infrared light include a method in which the image-forming material does not contain a medium such as water and the like, and specific examples of the method include an electrophotographic method.

Examples of the method for forming the fixed image using the image-forming material of the present exemplary embodiment include a method in which an image-forming material is applied onto a recording medium, and the image fixing is performed by irradiating the surface of the recording medium on which the image-forming material is applied, with laser light an output power of 1 J/cm² for 3 milliseconds.

Furthermore, the image-forming material of the present exemplary embodiment may be used, for example, for the purpose of recording the invisible information as described above.

The invisible information recorded using the image-forming material of the present exemplary embodiment may be read by using a semiconductor laser or light-emitting diode whose emission wavelength is within a range of, for example, more than 750 nm and equal to or less than 1000 nm as a light source for optical reading and using a general-purpose light-receiving device having high spectral sensitivity to near-infrared light. Examples of the light-receiving device include a light-receiving device by silicone (CCD or the like).

In the case where the image-forming material of the present exemplary embodiment is used in the recording of the invisible information, it may satisfy the conditions represented by the following formulae (6) and (7) shown below. It is thought that when the conditions represented by the following formulae (6) and (7) are satisfied, both invisibility of information and easy readability of the invisible information may be achieved.

$$0 \leq \Delta E \leq 7 \quad \text{Formula (6)}$$

$$(100-R) \geq 90 \quad \text{Formula (7)}$$

In the formula (6), $\Delta E$ represents the color difference according to the CIE 1976 L*a*b* color system represented by the following formula (8), and in the formula (7), R (unit: %) represents a reflectance of infrared rays at a wavelength of 820 nm in the image portion.

$$\Delta E = \sqrt{(L_1-L_2)^2 + (a_1-a_2)^2 + (b_1-b_2)^2} \quad (8)$$

In the formula (8), $L_1$, $a_1$, and $b_1$ represent the values of L, a, and b of the recording medium surface before image formation, respectively; and $L_2$, $a_2$, and $b_2$ represent the values of L, a, and b of an image portion, respectively, when a fixed image is formed on the recording medium surface with the image-forming material in an application amount of 4 g/m².

$L_1$, $a_1$, $b_1$, $L_2$, $a_2$, and $b_2$ can be obtained by using a reflection spectrodensitometer. In the present exemplary embodiment, these are measured using, for example, X-rite 939 manufactured by X-Rite, Inc., as a reflection spectrodensitometer.

EXAMPLES

Hereinbelow, the present exemplary embodiment will be described in detail with reference to Examples. However, the present exemplary embodiment is not intended to be limited to the Examples listed below.

Example 1

<Preparation of Perimidine-Based Squarylium Dye IA>

A mixed solution of 4.8 g (98%, 30 mmol) of 1,8-diaminonaphthalene, 3.9 g (98%, 30 mmol) of 2,6-dimethyl-4-heptanone, 40 mg (0.2 mmol) of p-toluenesulfonic acid monohydrate, and 45 ml of toluene is heated with stirring under a nitrogen gas atmosphere, and refluxed at 110° C. for 7 hours. The water generated during the reaction is removed by azeotropic distillation. After the completion of the reaction, the toluene is distilled off, and the obtained dark brown solid is extracted with acetone, purified by recrystallization from a mixed solvent of acetone and ethanol, and dried to obtain 7.625 g (yield 90%) of a perimidine intermediate (a).

To the obtained perimidine intermediate (a) is added a mixed solution of 1.4 g (12 mmol) of 3,4-dihydroxycyclobuta-3-ene-1,2-dione, 40 ml of n-butanol, and 60 ml of toluene, and the mixture is heated with stirring under a nitrogen gas atmosphere, and refluxed at 105° C. for 3 hours. The water generated during the reaction is removed by azeotropic distillation. After the completion of the reaction, the solvent is distilled off under a nitrogen gas atmosphere, and the obtained reaction mixture is stirred while adding 120 ml of n-hexane. The resulting black-brown precipitate is filtered by suction, washed with n-hexane, and dried to obtain a black-brown solid. This solid is washed with ethanol to obtain 6.2 g (yield 80%) of a perimidine-based squarylium dye IA that is a compound represented by Formula (I).

The compound (perimidine-based squarylium dye IA) thus obtained as described above is measured by an infrared absorption spectrum (KBr tablet method), 1H-NMR, and $^{13}$C-NMR. The results are shown below.

—Infrared Absorption Spectrum (KBr Tablet Method)—
  vmax=3392, 2954, 1617, 1577, 1541, 1456, 1367, 1309, 1226, 1132, 962, 933, 889, 818, 781, 757, 710, 679, 634, 590, 486, 418 cm$^{-1}$
—1H-NMR Spectrum (DMSO-d$_6$)—
  δ=10.46, 10.42 (d, 2H, NH); 7.81, 7.78 (d, 2H, H$_{arom}$); 7.38, 7.36, 7.33, 7.31 (m, 2H, H$_{arom}$); 7.20 (m, 2H, NH); 6.76, 6.73 (m, 4H, H$_{arom}$); 6.51, 6.49 (m, 2H, H$_{arom}$); 1.99 (m, 4H, CH); 1.76, 1.73, 1.69, 1.64 (m, 8H, CH$_2$); 0.94 (m, 24H, CH$_3$)
—$_{13}$C-NMR Spectrum (DMSO-d$_6$)—
  δ=149.31, 144.95, 133.95, 117.41, 48.56, 24.40, 23.19, 21.90

<Preparation of Specific Dye 1>

The perimidine-based squarylium dye IA obtained is subjected to isomer separation by column chromatography as follows to obtain a specific dye 1.

Specifically, first, silica gel 60N (spherical, neutral, particle diameter 63 to 210 μm) is used as a material for a filler, to prepare a packed cylindrical column having an inner diameter of 65 mm and a length of 15 cm. Next, n-hexane is used as a developing solvent to rinse the column filler, and then a dye solution in which 1 g of the perimidine-based squarylium dye to be separated is dissolved in 15 ml of acetone is adhered to about 40 g of the silica gel 60N, followed by volatilization of acetone, and the residue is added to the packed column. Thereafter, n-hexane, a mixed solvent including 90% by volume of n-hexane and 10% of THF, a mixed solvent including 85% by volume of n-hexane and 15% by volume of THF, or a mixed solvent including 80% by volume of n-hexane and 20% by volume of THF are flowed sequentially as developing solvents into the column, the components showing a maximum absorption at 802 nm to 808 nm are collected while checking the absorption of the eluate, the solvent is removed by distillation under reduced pressure, and a thus obtained black-brown solid is further recrystallized from a mixed solvent of acetone and n-hexane to obtain 0.5 g of a specific dye 1.

The specific dye 1 thus obtained is subjected to HPLC analysis by the above method. The proportion of the peak area of the peak A (the area proportion of the peak A), the proportion of the peak area of the peak B (the area proportion of the peak B), and the proportion of the peak area of the peak C (the area proportion of the peak C), relative to the sum of the peak area of the peak A, the peak B, and the peak C, are shown in Table 1.

Furthermore, the specific dye 1 thus obtained is subjected to absorption spectrum measurement by the method. The maximum absorption wavelength, the value of A$_{MAX}$, and the values of relative absorbances at 845 nm, 750 nm, 410 nm, and 345 nm are shown in Table 1.

<Preparation of Image-forming Material 1>
—Microparticulation (Formation of Pigment) Treatment—

50 mg of the specific dye 1, 0.5 mL of tetrahydrofuran (THF), and 10 g of zirconia beads having a diameter of 1 mm are put into a vessel for ball milling, and subjected to a milling treatment for 1 hour. Water is added into the vessel for ball milling, and the solution is filtered through a filter, and a microparticulated specific dye 1 is recovered. The volume-weighted average particle diameter thereof is 90 nm.
—Production of Slurry—

4.8 mg of the microparticulated specific dye 1, 24 μL of a 12% aqueous sodium dodecylbenzenesulfonate solution, and 2.88 ml of distilled water are mixed, and subjected to ultrasonic dispersion to prepare a slurry (using a ¼-inch horn at an ultrasonic output of from 4 to 5 W for an irradiation time of 30 minutes). The sample concentration in the slurry is 0.165% by mass.

—Production of Slurry-Coated Paper (Latex Patch for Evaluation)—

A mixed solution of 37 μL of the slurry thus obtained as described above (sample concentration: 0.165% by mass), 15 μL of a 40% by mass latex solution (40% by mass aqueous styrene-n-butyl acrylate copolymer solution), and 5 ml of distilled water is dispersed using an Ultra-Turrax to provide a mixed slurry. To the obtained mixed slurry is added 24 μL of a 10% aqueous polyaluminum chloride solution (PAC) as a flocculant, and thus a pseudo toner dispersion liquid is provided.

The obtained pseudo toner dispersion liquid is filtered through a 220-nm filter to obtain an image-forming material 1 (dye latex complex). Further, the image-forming material 1 is a complex showing the same color characteristics as the toner. The image-forming material 1 is air-dried, and then subjected to thermocompression (120° C.) to prepare a latex patch for evaluation (image for evaluation), in which the toner load is 4.5 g/m$^2$, the amount of the dye per unit area (the amount of the specific dye 1 in the present Example) is 0.045 g/m$^2$ (corresponding to 1% by mass of the content of the specific dye 1 in the image-forming material 1).

<Evaluation of Image-forming Material 1>
—Evaluation of Latex Patch for Evaluation—

The latex patch for evaluation obtained is measured using a reflection spectrodensitometer (X-rite 939 manufactured by X-Rite, Inc.); and the color difference (ΔE) in the CIE 1976 L*a*b* color system represented by the formula (8) and the reflectance (R) of infrared rays at a wavelength of 820 nm in the image portion are determined. The results are shown in Table 2. Further, a lower value of the reflectance of the infrared rays indicates a larger amount of infrared absorption.

Example 2

<Preparation of Specific Dye 2>

In the same manner as in the preparation of the perimidine-based squarylium dye IA except that 17 ml of n-hexanol and 83 ml of toluene are used instead of 40 ml of n-butanol and 60 ml of toluene in the "Preparation of Perimidine-Based Squarylium Dye IA" in Example 1, a specific dye 2 is obtained.

The specific dye 2 thus obtained is subjected to HPLC analysis by the above method. The area proportions of the peak A, the peak B, and the peak C are shown in Table 1.

Further, the specific dye 2 thus obtained is subjected to absorption spectrum measurement by the above method. The maximum absorption wavelength, the value of A$_{MAX}$, and the values of relative absorbances at 845 nm, 750 nm, 410 nm, and 345 nm are shown in Table 1.

<Preparation of Image-forming Material 2>
In the same manner as for the image-forming material 1 except that the specific dye 2 is used instead of the specific dye 1, an image-forming material 2 is prepared.

Furthermore, in the same manner as in Example 1 except that the image-forming material 2 is used instead of the image-forming material 1, evaluation (measurement of color difference and infrared reflectance) of the image-forming material 2 is carried out. The results are shown in Table 2.

Example 3

<Preparation of Specific Dye 3>
In the same manner as in the preparation of the perimidine-based squarylium dye IA except that 30 ml of n-hexanol and 70 ml of toluene are used instead of 40 ml of n-butanol and 60 ml of toluene in the "Preparation of Perimidine-Based Squarylium Dye IA" in Example 1, a specific dye 3 is obtained.

The specific dye 3 thus obtained is subjected to HPLC analysis by the above method. The area proportions of the peak A, the peak B, and the peak C are shown in Table 1.

Further, the specific dye 3 thus obtained is subjected to absorption spectrum measurement by the above method. The maximum absorption wavelength, the value of $A_{MAX}$, and the values of relative absorbances at 845 nm, 750 nm, 410 nm, and 345 nm are shown in Table 1.

<Preparation of Image-forming Material 3>
In the same manner as for the image-forming material 1 except that the specific dye 3 is used instead of the specific dye 1, an image-forming material 3 is prepared.

Furthermore, in the same manner as in Example 1 except that the image-forming material 3 is used instead of the image-forming material 1, evaluation (measurement of color difference and infrared reflectance) of the image-forming material 3 is carried out. The results are shown in Table 2.

Comparative Example 1

<Preparation of Perimidine-Based Squarylium Dye IB>
In the same manner as in the preparation of the perimidine-based squarylium dye IA except that 35 ml of n-hexanol and 65 ml of toluene are used instead of 40 ml of n-butanol and 60 ml of toluene in the "Preparation of Perimidine-Based Squarylium Dye IA" in Example 1, a perimidine-based squarylium dye IB is obtained.

The perimidine-based squarylium dye IB thus obtained is subjected to HPLC analysis by the above method. The area proportions of the peak A, the peak B, and the peak C are shown in Table 1.

Further, the perimidine-based squarylium dye IB thus obtained is subjected to absorption spectrum measurement by the above method. The maximum absorption wavelength, the value of $A_{MAX}$, and the values of relative absorbances at 845 nm, 750 nm, 410 nm, and 345 nm are shown in Table 1.

<Preparation of Image-forming Material 4>
In the same manner as for the image-forming material 1 except that the perimidine-based squarylium dye IB is used instead of the specific dye 1, an image-forming material 4 is prepared.

Furthermore, in the same manner as in Example 1 except that the image-forming material 4 is used instead of the image-forming material 1, evaluation (measurement of color difference and infrared reflectance) of the image-forming material 4 is carried out. The results are shown in Table 2.

Comparative Example 2

The perimidine-based squarylium dye IA obtained by "Preparation of Perimidine-Based Squarylium Dye IA" in Example 1 is used as it is.

The perimidine-based squarylium dye IA thus obtained is subjected to HPLC analysis by the above method. The area proportions of the peak A, the peak B, and the peak C are shown in Table 1.

Further, the perimidine-based squarylium dye IA thus obtained is subjected to absorption spectrum measurement by the above method. The maximum absorption wavelength, the value of $A_{MAX}$, and the values of relative absorbances at 845 nm, 750 nm, 410 nm, and 345 nm are shown in Table 1.

<Preparation of Image-forming Material 5>
In the same manner as for the image-forming material 1 except that the perimidine-based squarylium dye IA is used instead of the specific dye 1, an image-forming material 5 is prepared.

Furthermore, in the same manner as in Example 1 except that the image-forming material 5 is used instead of the image-forming material 1, evaluation (measurement of color difference and infrared reflectance) of the image-forming material 5 is carried out. The results are shown in Table 2.

TABLE 1

| | | HPLC analysis | | | Absorption spectrum (solvent: n-hexane:THF = 4:1) | | | | | |
|---|---|---|---|---|---|---|---|---|---|---|
| Example | Dye | Area proportion of peak A (%) | Area proportion of peak B (%) | Area proportion of peak C (%) | Maximum absorption wavelength (nm) | $A_{MAX}$ | Relative absorbance at 845 nm | Relative absorbance at 750 nm | Relative absorbance at 410 nm | Relative absorbance at 345 nm |
| Example 1 | Specific dye 1 | 99.7 | 0.3 | 0 | 805 | 1.322 | 0.047 | 0.19 | 0.040 | 0.047 |
| Example 2 | Specific dye 2 | 97.0 | 1.2 | 1.8 | 805 | 1.305 | 0.051 | 0.20 | 0.041 | 0.052 |
| Example 3 | Specific dye 3 | 95.0 | 2.0 | 3.0 | 805 | 1.293 | 0.053 | 0.20 | 0.042 | 0.055 |
| Comparative Example 1 | Dye IB | 94.0 | 2.2 | 3.8 | 805 | 1.286 | 0.064 | 0.22 | 0.053 | 0.067 |
| Comparative Example 2 | Dye IA | 81.0 | 2.6 | 16.4 | 805 | 1.179 | 0.15 | 0.29 | 0.074 | 0.12 |

TABLE 2

| Example | Dye | Color difference (ΔE) | Reflectance R (%) of infrared rays at 820 nm |
|---|---|---|---|
| Example 1 | Specific dye 1 | 5.3 | 5.70 |
| Example 2 | Specific dye 2 | 6.2 | 7.40 |
| Example 3 | Specific dye 3 | 6.7 | 9.60 |
| Comparative Example 1 | Dye IB | 7.8 | 12.50 |
| Comparative Example 2 | Dye IA | 10.3 | 22.28 |

As seen from the evaluation results shown in Table 1, the specific dyes of Examples have lower relative absorbances at 750 nm and 410 nm (that is, have lower absorption in the visible region) than the dyes of Comparative Examples.

Furthermore, as seen from the evaluation results shown in Table 2, with the image-forming materials of Examples, the ΔE value is lower and an image having a hardly-visible perimidine-based squarylium dye can be obtained, as compared with the image-forming materials of Comparative Examples.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A perimidine-based squarylium dye comprising a compound represented by Formula (1):

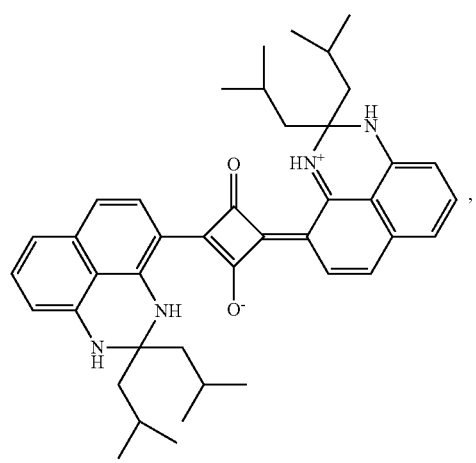

Formula (1)

wherein
95% by mole or more of the compound of Formula (1) is an isomer A, the isomer A being an isomer of a peak shown in the longest retention time among all peaks due to isomers obtained by analysis of the compound represented by Formula (1) by means of reversed-phase high-performance liquid chromatography; and
the compound of Formula (1) satisfies the following formulae:

$(A_{845}/A_{MAX}) \leq 0.059$, $(A_{750}/A_{MAX}) \leq 0.21$, $(A_{410}/A_{MAX}) \leq 0.043$, and $(A_{345}/A_{MAX}) \leq 0.063$, where $A_{MAX}$ represents an absorbance at a maximum absorption shown in the absorption wavelength in the range equal to or more than 802 nm and equal to or less than 808 nm, $A_{845}$ represents an absorbance of the absorption wavelength of 845 nm, $A_{750}$ represents an absorbance of the absorption wavelength of 750 nm, $A_{410}$ represents an absorbance of the absorption wavelength of 410 nm, and $A_{345}$ represents an absorbance of the absorption wavelength of 345 nm, in an absorption spectrum of a solution formed by dissolution of the compound in a mixed solvent comprising 80% by volume of n-hexane and 20% by volume of tetrahydrofuran.

2. The perimidine-based squarylium dye according to claim 1, wherein a proportion of the isomer A in the compound of Formula (1) is 99% by mole or more.

3. The perimidine-based squarylium dye according to claim 1, wherein the compound satisfies the following formulae:

$(A_{845}/A_{MAX}) \leq 0.051$, $(A_{750}/A_{MAX}) \leq 0.20$, $(A_{410}/A_{MAX}) \leq 0.041$, and $(A_{345}/A_{MAX}) \leq 0.062$.

4. A dye-containing composition, containing the perimidine-based squarylium dye according to claim 1.

5. A dye-containing composition, containing the perimidine-based squarylium dye according to claim 2.

6. A dye-containing composition, containing the perimidine-based squarylium dye according to claim 3.

7. The dye-containing composition according to claim 4, wherein the dye-containing composition is an image-forming material.

8. The dye-containing composition according to claim 7, wherein the perimidine-based squarylium dye is contained in an amount of from about 0.05% by mass to about 3% by mass.

* * * * *